United States Patent [19]

Buysch

[11] Patent Number: 4,764,310

[45] Date of Patent: Aug. 16, 1988

[54] PROCESS FOR THE PREPARATION OF AROMATIC CARBOXYLIC ACID CHLORIDES

[75] Inventor: Hans-Josef Buysch, Krefeld, Fed. Rep. of Germany

[73] Assignee: Bayer Aktiengesellschaft, Leverkusen, Fed. Rep. of Germany

[21] Appl. No.: 911,925

[22] Filed: Sep. 22, 1986

[30] Foreign Application Priority Data

Oct. 9, 1985 [DE] Fed. Rep. of Germany ....... 3535984

[51] Int. Cl.$^4$ ............................................... C07C 63/00
[52] U.S. Cl. ............................. 260/544 K; 260/544 P
[58] Field of Search ....................... 260/544 K, 544 P

[56] References Cited

U.S. PATENT DOCUMENTS

| 2,865,925 | 12/1958 | Toland | 568/877 |
| 3,346,594 | 10/1967 | Merijan et al. | 260/544 Y |
| 3,562,326 | 6/1976 | Semler et al. | 260/544 K |
| 4,308,216 | 12/1981 | Freitag et al. | 260/544 K |
| 4,322,373 | 3/1982 | Freitag et al. | 260/544 K |

OTHER PUBLICATIONS

Patai, Saul, *The Chemistry of Acyl Halides*, (1972), Interscience, Publ., p. 45.
Chemical Abstracts, Band 54, nr. 6, 25. Marz 1960, Spalte 5425, e-f, Columbus, Ohio, U.S.: L. Horner et al.: "Phosphorus Organic Compounds. XVII. Reaction with Triphenylphosphine dihalides; the Reaction Path of Halogen Introduction or Dehydration by Phosphorus Halides", & Ann. 62, 26–34, (1959).

*Primary Examiner*—Paul J. Killos
*Attorney, Agent, or Firm*—Sprung Horn Kramer & Woods

[57] ABSTRACT

Aromatic carboxylic acid chlorides can be prepared from alkyl esters of aromatic carboxylic acids by reaction of the alkyl esters with phosgene at 100°–300° C. in the presence of organophosphorus compounds. This reaction can also be carried out in the presence of an inert solvent.

8 Claims, No Drawings

PROCESS FOR THE PREPARATION OF AROMATIC CARBOXYLIC ACID CHLORIDES

The present invention relates to a process for the preparation of aromatic carboxylic acid chlorides by treatment of alkyl esters of aromatic carboxylic acids with phosgene in the presence of phosphorus compounds.

It is known from U.S. Pat. No. 2,865,959 that aromatic carboxylic acid chlorides can be prepared from esters of: aromatic carboxylic acids by reaction with chlorine in the presence of metal chlorides, such as iron trichloride, antimony trichloride or zinc chloride. In addition to the desired acid chlorides, hydrogen chloride and a large number of conversion products from the alcohol components of the esters are thereby formed. Examples of such conversion products are aldehydes, ketones, alcohols, olefines and alkyl mono- and alkyl dichlorides; methyl esters give formaldehyde as the first by-product.

Many of these conversion products are unstable under the reaction conditions. In particular, aldehydes and ketones are very reactive towards chlorine and, in addition to additional hydrogen chloride, give further aggressive, toxic products which irritate the mucous membrane. In the presence of the hydrogen chloride split off, carbonyl compounds can also undergo addition and condensation reactions, for example with the elimination of water. Overall, an abundance of various substances, which can be separated only with difficulty and which either remain in the reaction mixture or are discharged with the stream of waste gas, and in any case can be removed and rendered harmless only with the aid of extensive working up methods, is thus obtained.

It is known from DE-AS (German Published Specification) No. 2,158,551 that the associated dicarboxylic acid dichlorides can be obtained by chlorination of polyesters of aromatic dicarboxylic acids. In this process also, the abovementioned difficulties must be reckoned with.

Nuclear chlorination must furthermore be reckoned with in the two processes mentioned, especially if the metal chloride catalysts mentioned are used. Treatment of the hydrogen chloride formed in large amounts in the two processes is a further nuisance of the processes mentioned.

A process has been found for the preparation of aromatic carboxylic acid chlorides from alkyl esters of aromatic carboxylic acids, which is characterized in that the alkyl esters of aromatic carboxylic acids are treated with phosgene at 100°–300° C. in the presence of organophosphorus compounds and, if appropriate, in the presence of an inert solvent.

The reaction of the process according to the invention can generally be formulated as follows:

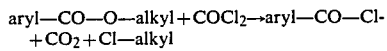

In addition to the desired acid chloride, carbon dioxide and the associated alkyl chloride, which is stable under the reaction conditions, is obtained in a high yield and can be used for a number of other industrial processes, are obtained.

Aryl in the above formulation is understood as a radical derived from an aromatic system. Examples of such aromatic systems are benzene, naphthalene, anthracene, phenanthrene and systems in which two benzene nuclei are connected by a bridge member, the bridge member representing, for example, a single bond, oxygen, sulphur, the sulphone group $-SO_2-$, the carbonyl group $-CO-$, a $C_1-C_6$-alkylidene radical or a $C_5-C_7$-cycloalkylidene radical. Examples of the systems last mentioned, formed by bridge members, are: diphenyl, diphenyl ether, diphenyl thioether, diphenyl sulphone, benzophenone, diphenylmethane, 2,2-diphenylpropane and 1,1-diphenyl-cyclohexane.

The aryl radicals originating from the systems mentioned can be substituted, for example by halogen, such as fluorine, chlorine, bromine or iodine, preferably fluorine, chlorine or bromine and particularly preferably chlorine; $C_1-C_4$-alkyl, such as methyl, ethyl, propyl, isopropyl, butyl or isobutyl, preferably methyl or ethyl; $C_1-C_4$-alkoxy, such as methoxy, ethoxy, propyloxy, isopropyloxy, butoxy or isobutoxy, preferably methoxy or ethoxy; nitro; or cyano.

The aryl radical can carry one or more of the substituents mentioned, and if appropriate also various substituents of the types mentioned.

The aryl radical furthermore carries one or more carboxylic acid functions, so that, if appropriate, the alkyl ester of aromatic carboxylic acids can be based on an aromatic monocarboxylic acid, dicarboxylic acid or polycarboxylic acid.

Examples of aromatic carboxylic acids in the esters to be reacted according to the invention are: benzoic acid, o-, m- and p-methylbenzoic acid, o-, m- and p-chlorobenzoic acid, tert.-butylbenzoic acid, methoxybenzoic acid, fluorobenzoic acid, bromobenzoic acid, nitrobenzoic acid, dimethylbenzoic acids, dichlorobenzoic acids, phthalic acid, isophthalic acid, terephthalic acid, naphthalenedicarboxylic acid, diphenyldicarboxylic acid, diphenyl ether-dicarboxylic acid, isophthalic acid, benzenetricarboxylic acids and benzenetetracarboxylic acids, in particular benzoic acid and iso- and terephthalic acid.

Alkyl in the above general formulation may be understood as an open-chain or cyclic alkyl.

Open-chain alkyl may be, for example, a $C_1-C_{18}$-, preferably $C_1-C_8$- and particularly preferably $C_1-C_4$-alkyl, such as methyl, ethyl, propyl, isopropyl, butyl, isobutyl, hexyl, octyl, dodecyl, palmityl or stearyl.

Cyclic alkyl may be, for example, $C_4-C_7$- and preferably $C_5-C_6$-cycloalkyl, such as cyclobutyl, cyclopentyl, cyclohexyl, cycloheptyl, methylcyclopentyl or methylcyclohexyl.

The alkyl radicals mentioned can be substituted, for example by $C_1-C_4$-alkyl or halogen, in the manner described above, and furthermore by phenyl, which can in turn be substituted by the substituents described above for aryl. Alkyl can furthermore be substituted by the hydroxyl group if conversion thereof into a chlorine substituent during the processing according to the invention is permitted.

The alkyl radical in the above general formulation furthermore also comprises alkylidene or cycloalkylidene radicals, so that the alcohol on which the alkyl esters of aromatic carboxylic acid to be reacted according to the invention are based can thus also be a di- or trialcohol, in addition to a monoalcohol.

The following alkyl esters of aromatic carboxylic acids can of course accordingly be reacted by the process according to the invention: monoesters of an aromatic monocarboxylic acid and a monoalkanol; diesters of an aromatic dicarboxylic acid and two molecules of a monoalkanol or, if appropriate, of two different monoalkanols; diesters of an alkanediol and two molecules of an aromatic carboxylic acid or, if appropriate, of two different aromatic carboxylic acids; triesters or even higher esters of aromatic tricarboxylic acids or even higher carboxylic acids and alkanols of the type mentioned; triesters of alkanetriols and aromatic carboxylic acids of the type mentioned; and finally oligoesters or polyesters of di- or polycarboxylic acids with alkanediols or -polyols. As an example of the case mentioned last, waste products from the production and processing of polyester, in particular polyethylene and polybutylene terephthalates, can be subjected to the process according to the invention, terephthalic acid dichloride and 1,4-dichlorobutane being obtained in the case of polybutylene phthalate. In each of the cases mentioned, all the ester groups present in the reaction mixture can react in the context according to the invention. Ester groups which have not reacted completely, for example polyesters which have not been completely degraded, can be added to a subsequent batch for renewed reaction according to the invention.

The process according to the invention is carried out in the presence of organophosphorus compounds of the formula $$\begin{matrix} R^1 & & X \\ & \diagdown & \diagup \\ R^2 & —P & \\ & \diagup & \diagdown \\ R^3 & & Y \end{matrix} \quad (I)$$

wherein $R^1$, $R^2$ and $R^3$ independently of one another can denote alkyl, cycloalkyl, aralkyl or aryl, or wherein $R^1$ and $R^2$, together with the phosphorus atom, can form a 5- 6-membered ring, and furthermore $R^1$ can also denote halogen, and X and Y represent identical or different halogen, but can also together denote double-bonded oxygen, double-bonded sulphur, double-bonded nitrogen =N—$R^4$, wherein $R^4$ denotes alkyl, cycloalkyl, aralkyl, aryl, acyl, aryloxycarbonyl, dialkylphosphonyl or diarylphosphonyl, preferably alkyl, aryl or acyl, or an electron pair, and furthermore X denotes alkyl, aralkyl, aryl or allyl, if Y simultaneously represents a positive partial charge on the phosphorus atom, a negative counterion, which, if appropriate, can also be allocated to X as a substituent if X denotes alkyl, aralkyl, aryl or allyl, being present in this case.

The organophosphorus compounds of the formula (I) thus include, for example, organophosphines (formula II), organophosphine oxides (III), organophosphine sulphides (IV), organophosphonium salts (V), organophosphorus-betaines (VI), dihalogeno-organophosphines (VII) and N-substituted organophosphine-imines (VIII).

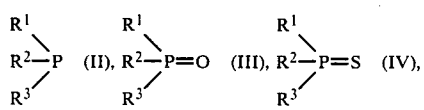

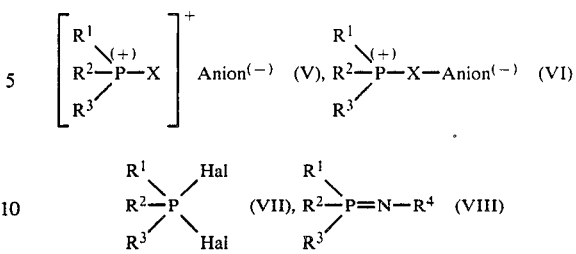

In the formulae (I) to (VIII), alkyl, aryl and halogen have the abovementioned meaning, alkyl also including cycloalkyl. Aralkyl which may be mentioned is, for example, benzyl, phenethyl, naphthylmethyl or naphthylethyl, preferably benzyl.

The radicals $R^1$, $R^2$, $R^3$ and X in the meaning of alkyl, aryl or aralkyl can be substituted in the manner described above. $R^1$ and $R^2$ together can also denote tetramethylene or pentamethylene, and together with the phosphorus atom can form a 5- or 6-membered ring.

Examples which may be mentioned of the anion in (V) or (VI) are: chloride, bromide, hydroxide, sulphate (1 equivalent), sulphonate and carboxylate.

Examples which may be mentioned of organophosphorus compounds which can be used according to the invention are: diphenylchlorophoshine, tributylphosphine, tris(cyanoethyl)-phosphine, dicylohexyldodecylphosphine, triphenylphosphine, tris-(p-chlorophenyl)-phosphine, 1-methyl-phospholine, triphenylbenzyl-phosphonium chloride, tributyl-allyl-phosphonium bromide, triphenylphosphine-carbomethoxymethylene, β-triphenylphosphonium propionate, phenyloxy-trimethylphosphonium chloride, β-triphenylphosphonium ethylsulphonate, triphenylphosphine hydroxide chloride, triethyl-carbonyloxyphenylchlorophosphine, 1,1-dichlorotriphenylphosphine, 1,1-dibromo-tris(cyanoethyl)phosphine, 1-phenyl-3-phospholine 1,1-dichloride, dimethyl-cyclohexylphosphine oxide, tris(chloropropyl)phosphine oxide, dimethylphenylphosphine oxide, tris-(p-cyanophenyl)-phosphine oxide, triphenylphosphine sulphide, trimethylphosphine sulphide, 1-methyl-3-phospholine 1-oxide, 1-phenyl-3-phospholine 1-oxide, tris(hydroxyethyl)-phosphine, triethyl-N-acetyl-phosphine-imine and triphenyl-N-phenyl-phosphine-imine.

Organophosphorus compounds of the formulae (II), (III) and (VI) are preferably employed; organophosphorus compounds of the formulae (II) and (III) are particularly preferably employed. Examples of such compounds are tributylphosphine, tris-(cyanoethyl)-phosphine, triphenylphosphine, tris-(4-chlorophenyl)-phosphine, triphenylphosphine oxide and β-triphenylphosphonium propionate, in particular triphenylphosphine and triphenylphosphine oxide.

Instead of one organophosphorus compound, it is also possible to use a mixture of several. The organophosphorus compound or a mixture of several remaining as the distillation residue during working up of the reaction mixture can likewise be reused for another batch.

The amount of catalyst is 0.01–15% by weight, preferably 0.1–10% by weight and particularly preferably 0.3–7% by weight, in all cases based on the amount of alkyl ester of aromatic carboxylic acid employed.

The process according to the invention can be carried out with or without a solvent. Suitable solvents are substances which are inert under the reaction conditions and can be separated off as easily as possible, for example aliphatic and aromatic hydrocarbons, aliphatic and aromatic halogenohydrocarbons and aliphatic and aromatic nitriles, such as white spirit, toluene, xylene, methylene chloride, trichloroethylene, dichlorobenzene, chloronaphthalene, diphenyl ether and benzonitrile. Acid chlorides, especially the aromatic carboxylic acid chloride formed in carrying out the process according to the invention, are furthermore possible as solvents which are inert under the reaction conditions and can easily be separated off.

The process according to the invention is carried out at a temperature of 100°–300° C., preferably 130°–270° C. and particularly preferably 150°–250° C.

The process according to the invention can be carried out in a wide pressure range, for example under 0.1–50 bar, preferably 0.5–30 bar and particularly preferably 0.8–10 bar. The use of an increased pressure is in general necessary if a low-boiling substrate or solvent is employed.

Phosgene is required in the process according to the invention in an amount of at least 1 mol per ester group for substantially bringing the reaction to completion. However, phosgene can also be employed in an excess of up to 100 mol, preferably up to 50 mol, per ester group. The excess of phosgene which is not consumed can be reused in a subsequent batch. The phosgene can be fed into the reaction vessel in liquid or gaseous form. Liquid phosgene can in principle also be used as a solution in one of the solvents mentioned; gaseous phosgene can likewise be used as a mixture with an inert gas, such as nitrogen, argon or carbon dioxide.

The process according to the invention can be carried out discontinuously or continuously. In both cases gaseous phosgene can advantageously be used in a bubble column apparatus. In the continuous procedure, for example, the phosgene-containing waste gas from the first bubble column is advantageously passed through further subsequent bubble columns. The last bubble column is then charged with fresh carboxylic acid ester and the overflow of one bubble column is introduced at the foot of the next. A waste gas which is virtually free from phosgene and essentially consists of carbon dioxide and which, after simple purification from entrained traces of carboxylic acid chloride, alkyl chloride and, if appropriate, solvent, can either be used as $CO_2$ or released into the atmosphere is obtained in this manner at the head of the last bubble column.

EXAMPLE 1

A mixture of 150 g of di-n-hexyl terephthalate and 7.5 g of triphenylphosphine oxide was melted in a cylindrical apparatus of 250 ml capacity and gassed with phosgene from the bottom through a frit under normal pressure. The temperature was kept between 170° and 190° C. The waste gas was passed through a cold trap kept at about 10° C. After 25 hours, the reaction mixture contained, in addition to unreacted di-n-hexyl terephthalate, 21.2 g of n-hexyl terephthalate chloride and 52.6 g of terephthalic acid dichloride. 64.6 g of n-hexyl chloride (91% of the theoretical amount, based on the acid ester chloride and acid dichloride formed) were to be found in the cold trap.

EXAMPLE 2

A mixture of 150 g of dimethyl terephthalate and 7 g of triphenylphosphine oxide was gassed with phosgene as in Example 1. After 5 hours, the reaction mixture contained only 1.3% of dimethyl terephthalate and 1.3% of methyl terephthalate chloride. After 6–7 hours, the conversion was complete and terephthalic acid dichloride was obtained (>99% pure).

EXAMPLE 3

A solution of 100 g of polybutylene terephthalate with a molecular weight of about 25,000 and 5 g of triphenylphosphine oxide in 300 g of o-dichlorobenzene was gassed with phosgene at 170°–175° C. for 10 hours, as described in Example 1. The initially viscous solution rapidly became more thinly liquid. The cold trap and the reaction mixture contained, in addition to the o-dichlorobenzene, 1,4-dichlorobutane formed from the butylene radical. On distilling the reaction mixture, after the o-dichlorobenzene and 1,4-dichlorobutane, 33 g of terephthalic acid dichloride passed over, and, at 180°–230° C./1–2 mbar, 38 g of a mixture of chlorine-containing cleavage products, which were not characterized in more detail, passed over and were fed to a subsequent batch and increased the yield of 1,4-dichlorobutane and terephthalic acid dichloride there, and can thus be converted into these substances.

It will be understood that the specification and examples are illustrative but not limitative of the present invention and that other embodiments within the spirit and scope of the invention will suggest themselves to those skilled in the art.

What is claimed is:

1. A process for the preparation of an aromatic carboxylic acid chloride, wherein the alkyl ester of the aromatic carboxylic acid is treated with phosgene at 130°–270° C. in the presence of an organophosphorus compound.

2. A process according to claim 1, wherein the organophosphorus compound is an organophosphine or an organophosphine oxide.

3. A process according to claim 1, wherein the organophosphorus compound is triphenylphosphine oxide.

4. A process according to claim 1, wherein the reaction is carried out at 150°–250° C.

5. A process according to claim 1 wherein, 1–100 mol of phosgene are used per equivalent of the alkyl ester.

6. A process according to claim 1, wherein the reaction is carried out in the presence of an inert solvent.

7. A process according to claim 1, wherein the alkyl ester is polyalkylene terephthalate and the reaction is carried out in the presence of an inert solvent.

8. A process according to claim 1, wherein the reaction is carried out continuously in a bubble column apparatus.

* * * * *